United States Patent
Purnell

[19]
[11] Patent Number: 5,961,512
[45] Date of Patent: *Oct. 5, 1999

[54] APPARATUS AND METHOD FOR POSITIONING A HUMAN ARM FOR SHOULDER SURGERY

[76] Inventor: Michael B. Purnell, 3508 Wycliffe Dr., Modesto, Calif. 95355

[*] Notice: This patent issued on a continued prosecution application filed under 37 CFR 1.53(d), and is subject to the twenty year patent term provisions of 35 U.S.C. 154(a)(2).

[21] Appl. No.: 08/884,007

[22] Filed: Jun. 27, 1997

[51] Int. Cl.⁶ .................................................. A61B 17/00
[52] U.S. Cl. .............................................. 606/1; 606/241
[58] Field of Search ............................... 606/1, 241, 243, 606/244, 242

[56] References Cited

U.S. PATENT DOCUMENTS

| | | | |
|---|---|---|---|
| 4,579,324 | 4/1986 | McConnell | 269/328 |
| 4,616,813 | 10/1986 | McConnell | 269/328 |
| 4,624,458 | 11/1986 | Fendrik | 606/243 |
| 4,702,465 | 10/1987 | McConnell | 269/328 |
| 5,501,656 | 3/1996 | Homma et al. | 606/241 |
| 5,509,894 | 4/1996 | Mason et al. | 606/241 |

OTHER PUBLICATIONS

"The Arthroscopy Traction System That's Positioned For Surgical Success, The 3–Point Shoulder Distraction System and Star Sleeve From Arthrex", Arthrex, 6 pages.
The McConnell System, 6 pages.

*Primary Examiner*—Michael Buiz
*Assistant Examiner*—Kevin Truong
*Attorney, Agent, or Firm*—Pandiscio & Pandiscio

[57] ABSTRACT

Apparatus for positioning a human arm for shoulder surgery which includes a clamp for attaching the apparatus to a support, a bracket movably mounted in the clamp, and a forearm pad movably mounted on the bracket and adapted to support the forearm portion of the human arm. A pulley support arm is movably mounted on the bracket and a pulley is mounted on the pulley arm. An upper arm cuff is provided for attachment to the upper arm portion of the human arm. A flexible strand is connected at an upper end to the cuff, extends along the pulley and, at a lower end thereof, receives a selected weight. The weight, in response to gravity, puts tension on the strand which in turn pulls the cuff, and thereby the human upper arm, outwardly from the body to which the arm is appended.

21 Claims, 7 Drawing Sheets

APPARATUS AND METHOD FOR POSITIONING A HUMAN ARM FOR SHOULDER SURGERY

FIELD OF THE INVENTION

This invention relates to surgical traction systems and methods generally, and more particularly to a novel traction system and method for positioning a human arm for shoulder surgery.

BACKGROUND OF THE INVENTION

Traditionally, shoulder surgery has been performed with the patient lying in a generally horizontal (or lateral) position on an operating table. A traction apparatus is used to pull the shoulder upwardly. The pulling force is typically applied to the patient's hand, such that the entire arm is distended in order to distend the patient's shoulder joint.

More recently, shoulder surgery has been performed with the patient positioned in a generally sitting position, wherein the patient's entire shoulder is exposed and accessible, and wherein the patient's shoulder is disposed in a more conventional anatomic position (i.e., so that "up" is "up"). Unfortunately, however, there is currently no traction or positioning apparatus for use with a sitting patient. The traditional traction devices discussed above are all arranged so as to pull the patient's shoulder upwardly, whereas when the patient is in the sitting position, it is desirable that the shoulder be pulled downwardly. Furthermore, the traditional traction devices discussed above do not allow for specific control of all three planes of motion.

Thus, there is the need for a new traction and/or positioning apparatus for use with patients undergoing shoulder surgery (either arthroscopic or open) while in a sitting position.

OBJECTS OF THE INVENTION

Accordingly, one object of the present invention is to provide a novel apparatus for positioning and/or tensioning a human arm for arthroscopic or open shoulder surgery while the patient is in a sitting position.

A further object of the present invention is to provide such an apparatus wherein the pulling force is applied to the patient's shoulder, rather than to the patient's hand.

A still further object of the present invention is to provide a novel method for tensioning and/or positioning a human arm for shoulder surgery while the patient is in a sitting position, wherein the shoulder may be pulled downwardly and laterally and with rotational control, and wherein the pulling force is applied to the patient's shoulder.

SUMMARY OF THE INVENTION

The above and other objects of the present invention are addressed by the provision and use of a novel apparatus for positioning and tensioning a human arm for shoulder surgery. The apparatus comprises a planar member for receiving, in a sitting position, the human patient to which the arm is appended, a clamp fixed to the planar member, and a bracket mounted on the clamp and having a portion extending laterally from the planar member in a plane generally parallel to a plane of the planar member. A pulley support arm is connected to the bracket's laterally-extending portion and extends transversely of the bracket's laterally-extending portion and upwardly toward a level generally alongside an upper portion of the patient's arm. A pulley is mounted on the pulley support arm. An upper arm cuff is provided for attachment to the upper portion of the patient's arm. The apparatus includes a flexible strand adapted for fixing, at a first end thereof, to the cuff, for riding along the pulley, and for receiving, at a second end thereof, a selected weight. A first portion of the strand is operative for fixing to the cuff and for pulling the cuff, and thereby the upper portion of the patient's arm. A second portion of the strand extends from the pulley and is adapted to receive the selected weight and to hang downwardly so as to put tension on the strand's first portion in response to the pull of gravity on the weight.

The objects of the present invention are further addressed by the provision and use of a novel method for positioning and tensioning a human arm for shoulder surgery, the method comprising the steps of providing an apparatus as described immediately above, seating the human patient, to which the arm is appended, on the planar member, and attaching the clamp to the planar member. The method further includes attaching the upper arm cuff to the upper portion of the patient's arm, attaching the first portion of the strand to the cuff, and attaching the selected weight to the second portion of the strand, so as to exert the desired tension on the upper portion of the patient's arm.

BRIEF DESCRIPTION OF THE DRAWINGS

The above and other objects and features of the present invention will be more fully disclosed or rendered obvious by the following detailed description of the preferred embodiments of the invention, which are to be considered together with the accompanying drawings wherein like numbers refer to like parts, and further wherein.

DETAILED DESCRIPTION OF THE PREFERRED EMBODIMENTS

Figure 1:
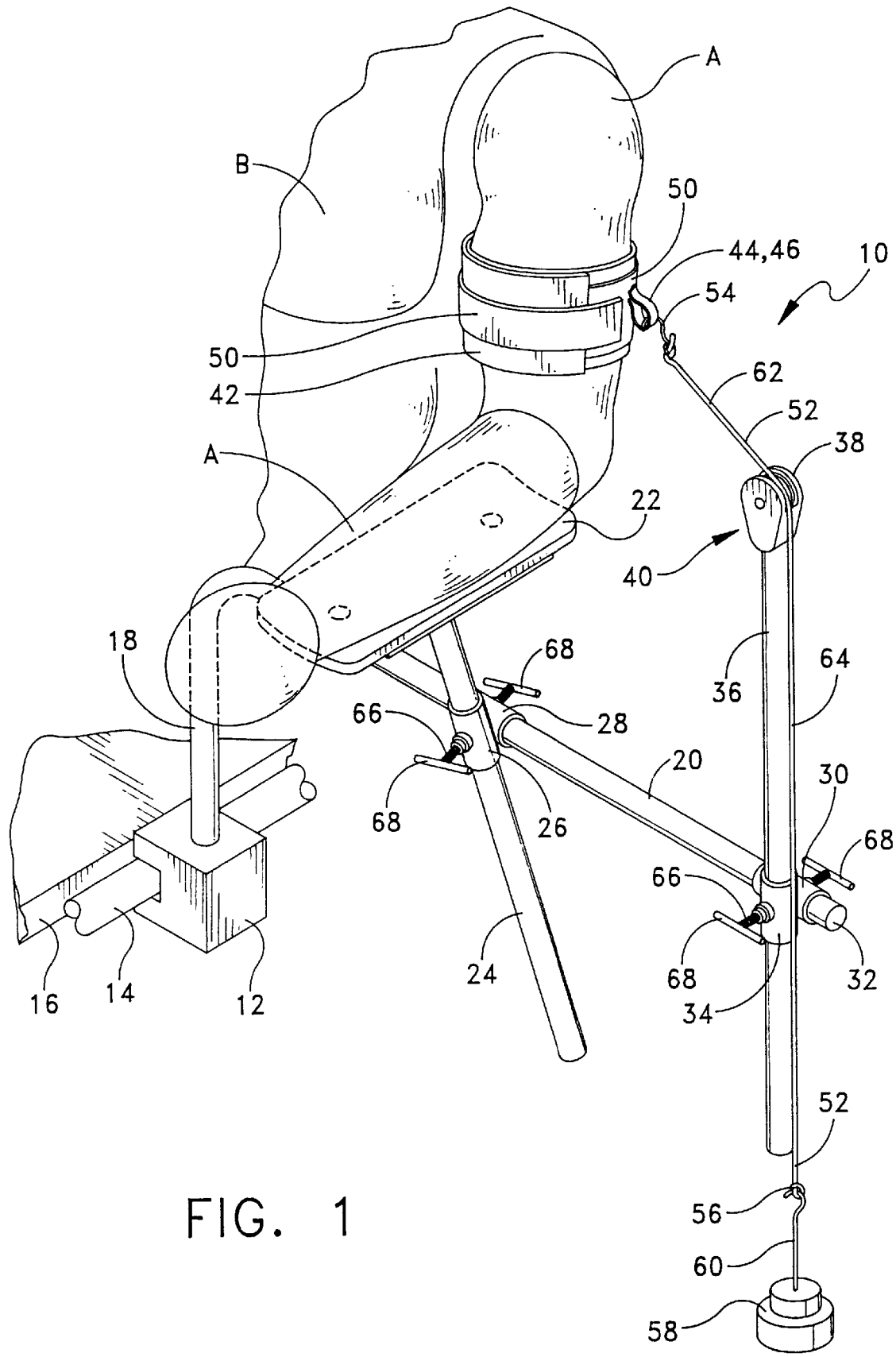
FIG. 1 is a perspective view of one form of apparatus illustrative of one embodiment of the invention.
Figure 2:
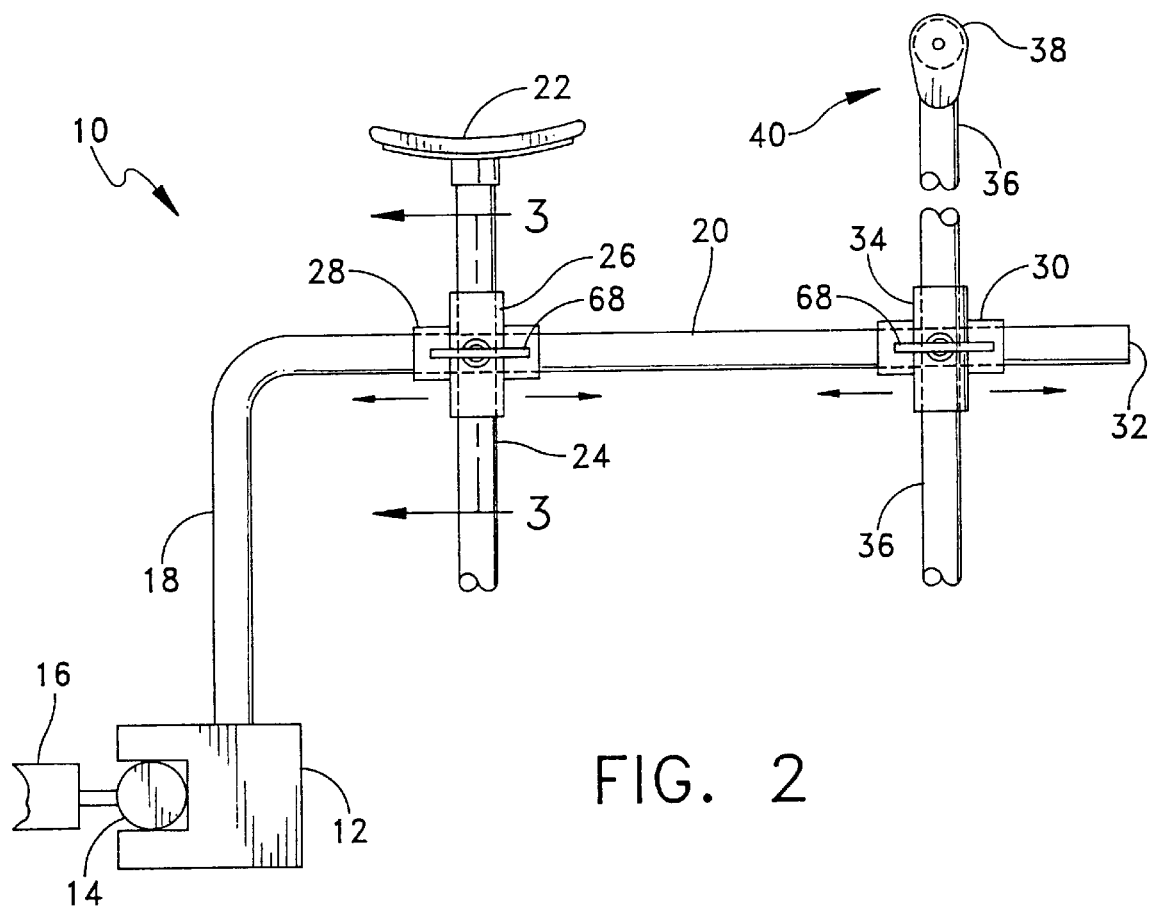
FIG. 2 is a front elevational view of a portion of the apparatus of FIG. 1.
Figure 3:
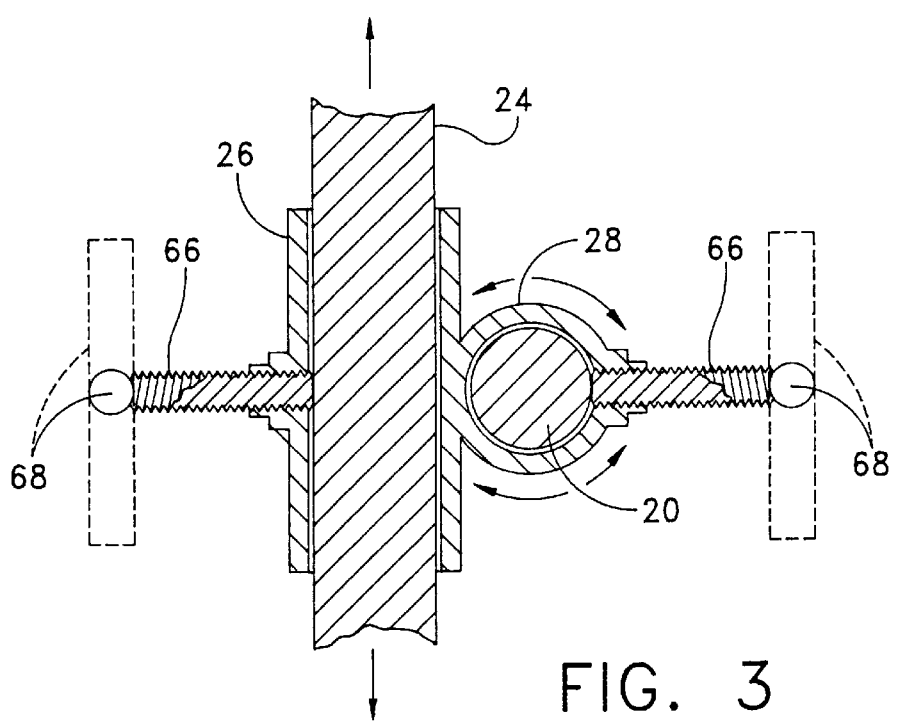
FIG. 3 is a generally sectional view taken along line 3—3 of FIG. 2, with the figure being in part elevational and in part diagrammatic.

Referring first to FIGS. 1–3, it will be seen that an illustrative apparatus 10 for positioning the arm A of a patient B for shoulder surgery includes a clamp 12 for attaching the apparatus to a rail 14 which is fixed to an operating table 16. Pivotally mounted on clamp 12 is a bracket 18 which is rotatively movable in a plane parallel to a plane of the operating table 16. Bracket 18 includes a generally horizontal portion 20 on which is mounted a forearm pad 22. The bracket portion 20 extends laterally from the table 16 and is movable in a plane generally parallel to the plane of table 16. Forearm pad 22 is supported by a forearm pad bar 24 which is releasably fixable in a tubular clamp 26. The tubular clamp 26, which supports forearm pad bar 24, is fixed to a second tubular clamp 28 which is in turn rotatively and slidably mounted on the bracket's horizontal portion 20 and which permits the forearm pad bar 24 to be tilted and moved toward and away from the table 16. The clamp 26 permits raising and lowering of the forearm pad 22, as well as pivotal movement thereof.

Thus, the forearm pad 22 can be selectively positioned by the pivotal movement of bracket 18 in clamp 12, pivotal and sliding movement of forearm pad bar 24, and the sliding and rotative movement of clamp 28 on bracket portion 20.

A tubular clamp 30 is disposed near a free end 32 of bracket portion 20. Clamp 30 is fixed to another tubular clamp 34. A pulley support arm 36 is mounted in clamp 34. Clamp 30 is slidably and rotatively movable on bracket portion 20, and pulley support arm 36 is slidably movable in clamp 34.

At least one pulley 38 is mounted on pulley support arm 36 on or near an upper end 40 of arm 36. Pulley 38 may be fixedly mounted to the upper end of arm 36. Alternatively, arm 36 may be pivotally mounted to the top of arm 36, whereby the pulley can rotate about the longitudinal axis of arm 36. Arm 36 is disposed in a generally vertical manner so as to place pulley 38 generally in the area of an upper portion of the patient's arm A, such as the biceps area.

Figure 4:
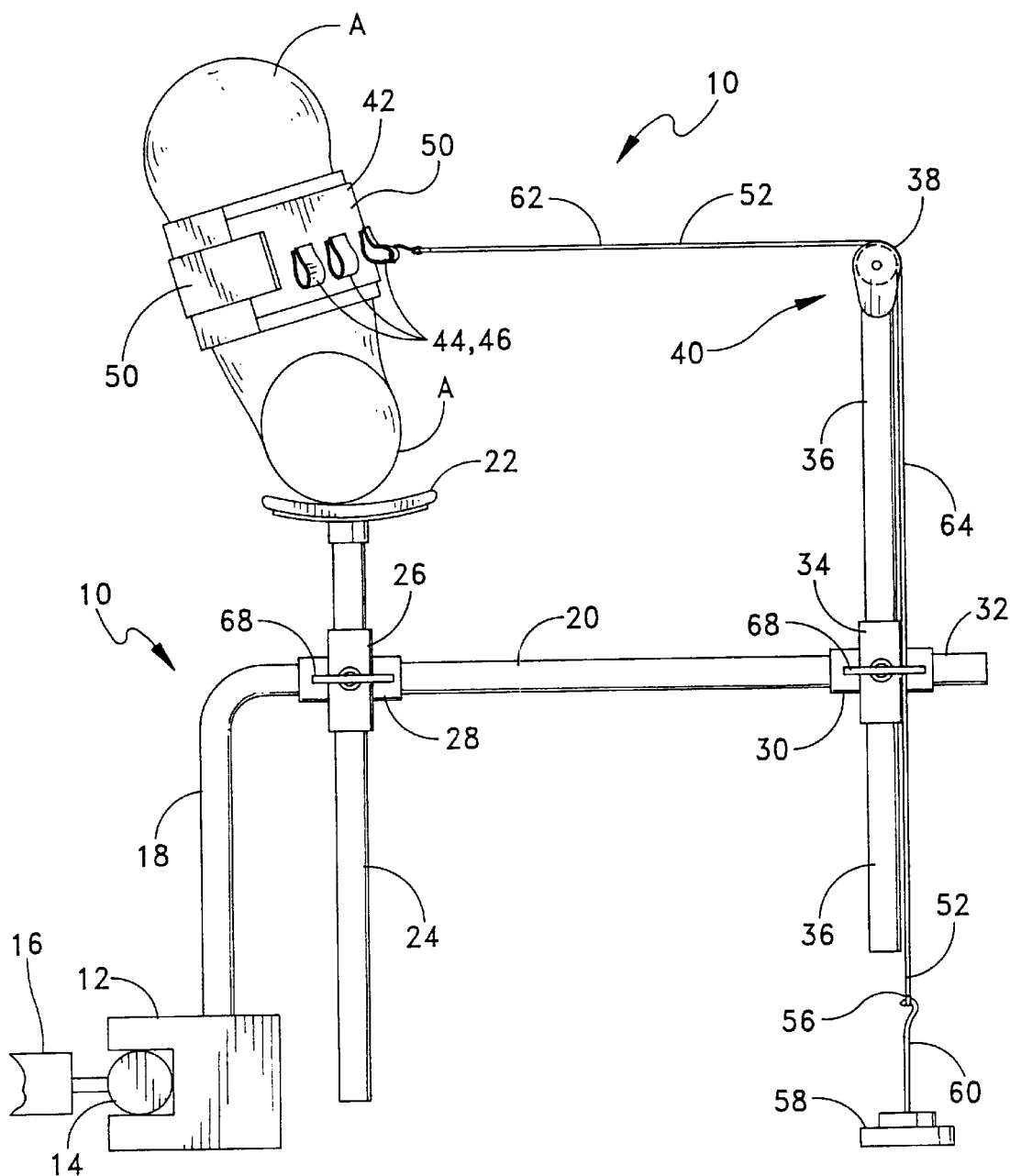
FIG. 4 is a front elevational view showing the apparatus of FIG. 1 in use.
Figure 5:
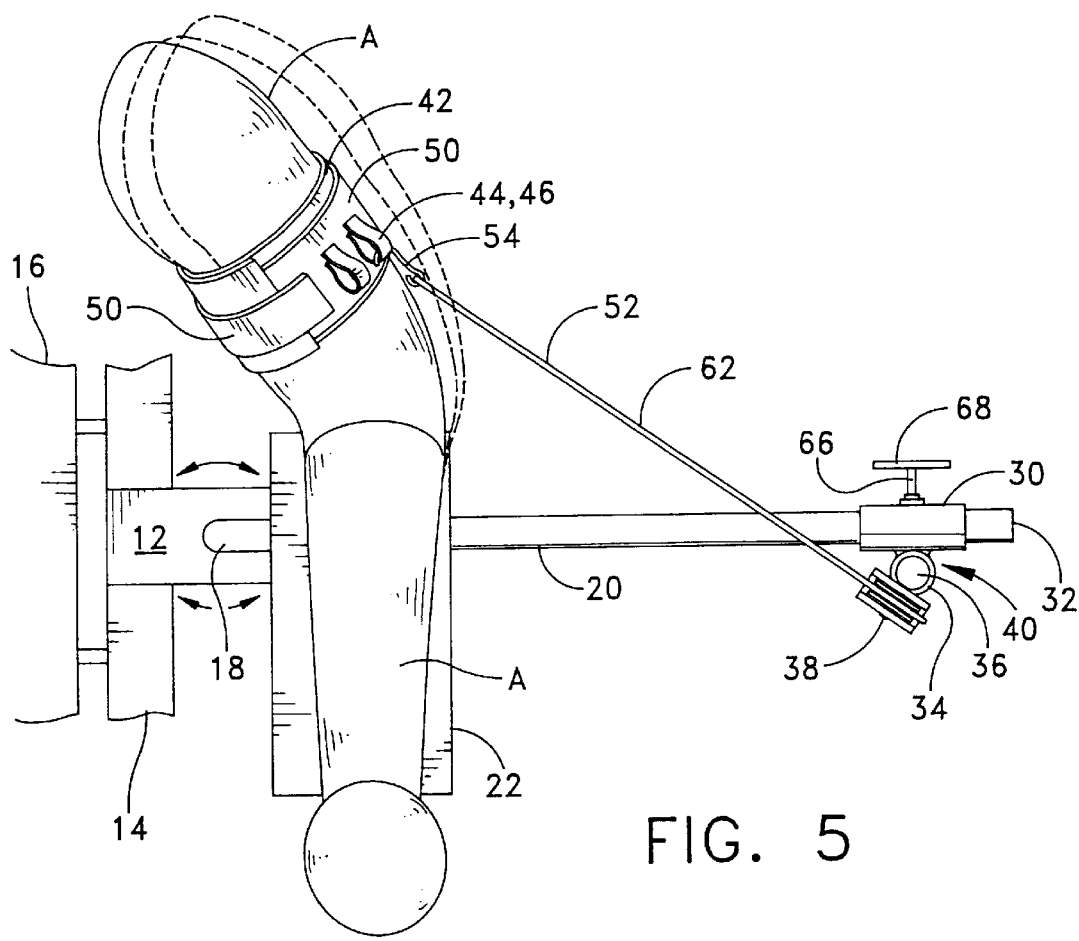
FIG. 5 is a top plan view showing the apparatus of FIG. 1 in use.
Figure 6:
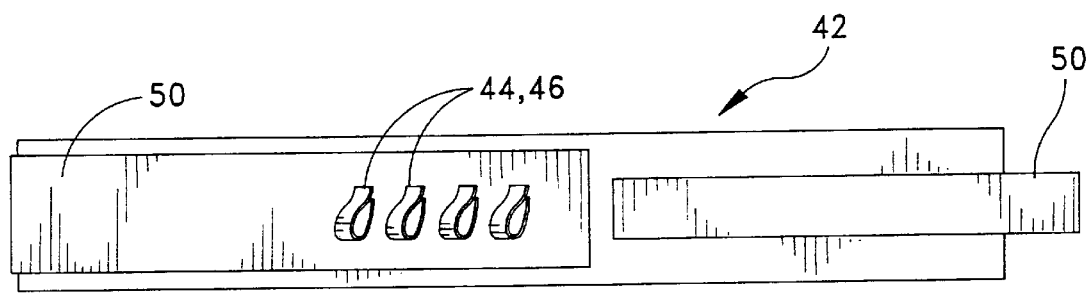
FIGS. 6 and 7 are top plan views of alternative embodiments of a cuff portion of the assembly of FIG. 1.
Figure 7:
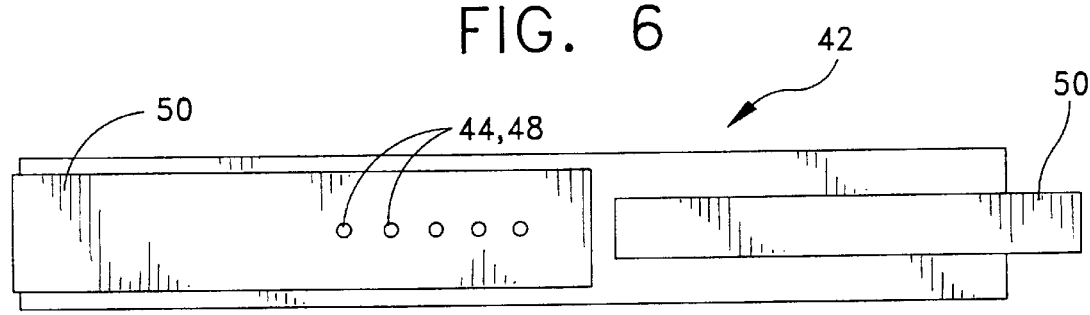

Apparatus 10 further includes an upper arm cuff 42 for encircling the upper arm portion, as shown in FIG. 1. Upper arm cuff 42 is provided with at least one connector 44 (FIG. 1), and preferably a series of connectors 44 (FIG. 4), disposed around the circumference of cuff 42. As shown in FIGS. 1, 4 and 6, connector 44 may comprise loops 46, but connector 44 may also comprise any other suitable connecting means, such as simply orifices 48, as shown in FIG. 7. The upper arm cuff 42 may be provided with hermaphroditic or hook-and-pile fasteners 50 (FIGS. 1 and 4–7) for quick and easy attachment and detachment.

A flexible strand 52 (FIG. 1), such as a wire or rope or the like, is provided, at an upper end thereof, with a connector 54 which is complementary to connector 44, such that the upper end of strand 52 may be readily connected to cuff 42. As shown in FIG. 1, the strand's upper end connector 54 may be a simple hook. At the lower end of strand 52, there is provided another connector 56, which may be a loop or the like, which is adapted to receive a weight member 58 fixed with a connector 60, which may be a hook or the like, which is complementary to the strand's lower end connector 56. The pulley 38 is adapted to support strand 52 between the upper and lower ends thereof. To that end, it is desirable that pulley 38 be disposed so that it will be aligned with the path of strand 52 as the strand extends away from arm A. This can be achieved either by (i) appropriately rotating pulley 38 atop arm 36, if pulley 38 is so rotatable relative to the arm, or (ii) by rotating the arm 36 relative to tubular clamp 34. Thus, the upper end of strand 52 is adapted to be fixed to cuff 42 such that a first portion 62 of strand 52 is operative to pull cuff 42 outwardly and downwardly from the patient's body B, to which arm A is appended. A second portion 64 of strand 52 is operative to receive a selected weight member 58 and to hang downwardly, so as to tension the strand's first portion 62 in response to the pull of gravity on weight member 58.

Figure 7A:
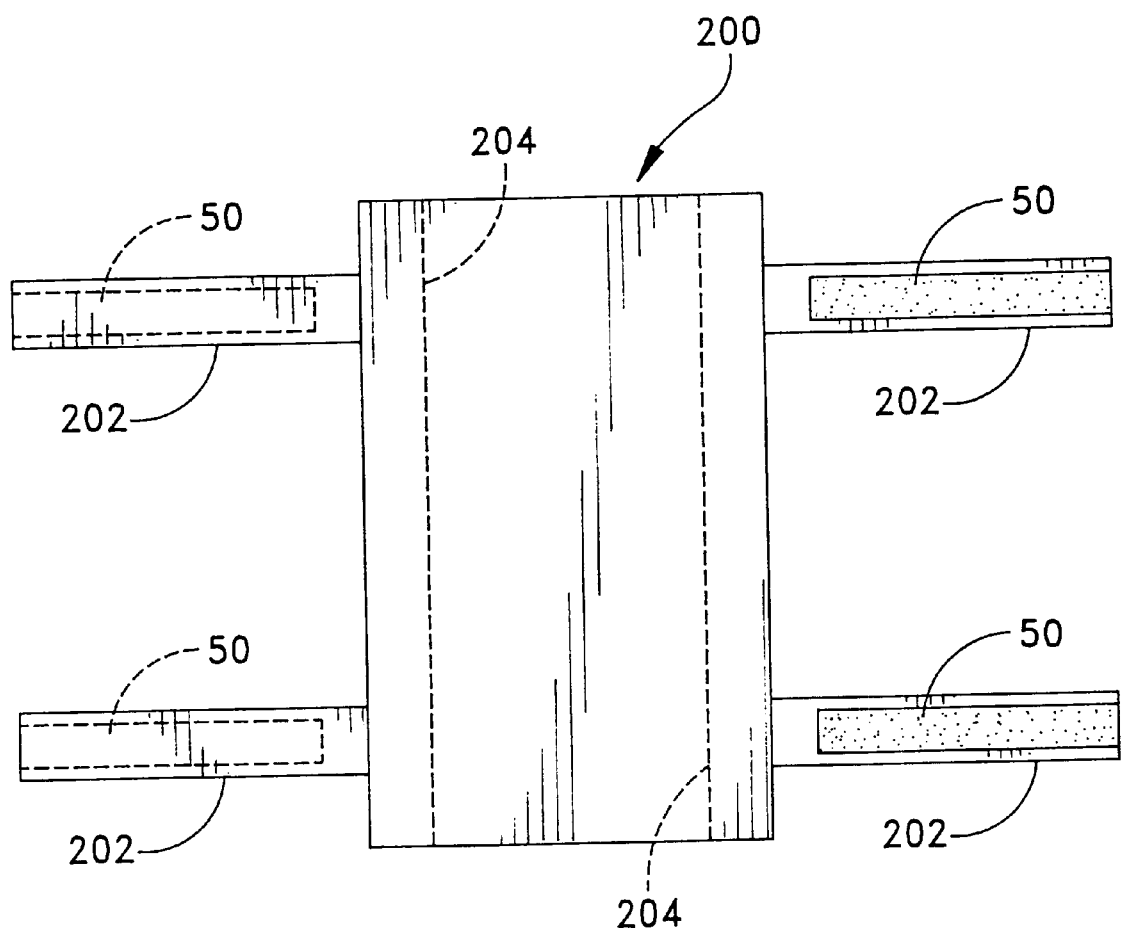
FIG. 7A is a top plan view of a sterilized, disposable covering which may be used in conjunction with the present invention.

In use, the patient's body B (from which arm A depends) is positioned on table 16 in a generally sitting position. If not done beforehand, apparatus 10 is fixed to table 16 by mounting clamp 12 on rail 14. By adjustment of bracket 18 and clamps 26 and 28, the positions of bracket portion 20 and forearm pad bar 24 are selected, thereby to selectively establish the position of forearm pad 22, and locked in place. Each of the clamps 26, 28, 30, and 34 is provided with a set or locking screw 66 and handle 68 (illustrated in FIGS. 1 and 3) by which the item within the clamp is locked in place. Forearm pad 22 may be covered with a sterilized, disposable covering 200 (FIG. 7A) which is then secured to forearm pad 22 by straps 202 which are equipped with hermaphroditic or hook-and-pile fasteners 50. Preferably creases 204 are pre-formed in disposable covering 200 so as to facilitate proper positioning of the covering on forearm pad 22. If desired, covering 200 may comprise a foam rubber type of material so as to render the covering 200 more comfortable to the patient. If desired, such foam rubber material may in turn be covered with an outer layer which is waterproof.

Forearm pad 22 may also be provided with appropriate straps or tie-downs (not shown) for securing the patient's forearm to the pad.

The upper arm cuff 42 is then placed around the patient's upper arm and fastened in place, as by joining of the fasteners 50. The upper end connector 54 of strand 52 is fixed to a selected cuff connector 44 (FIGS. 4 and 6). If rotation of the arm is not desired, the cuff connector 44 closest to pulley support arm 36 is connected to strand 52. By attaching strand 52 to a rearward connector 44, the arm may be rotated forwardly, the purpose of which is to relax the anterior shoulder soft tissues. The position of pulley support arm 36 is adjusted and locked in clamp 34. Apparatus arm 36 may be elevated such that the first portion 62 of stand 52 is generally horizontal, as shown in FIG. 4, or otherwise selected, as shown in FIG. 1, to effect tension in a desired direction.

The strand 52 is threaded through the pulley 38 and the selected weight member 58 is fixed to the lower end of strand 52. The pull of gravity on weight member 58 is translated into lateral tension which is exerted on cuff 42 and, thereby, on the patient's upper arm portion. This tension causes the patient's shoulder to be positioned in the desired manner, whereupon open or closed surgery can be conducted on the patient's shoulder joint.

Figure 8:
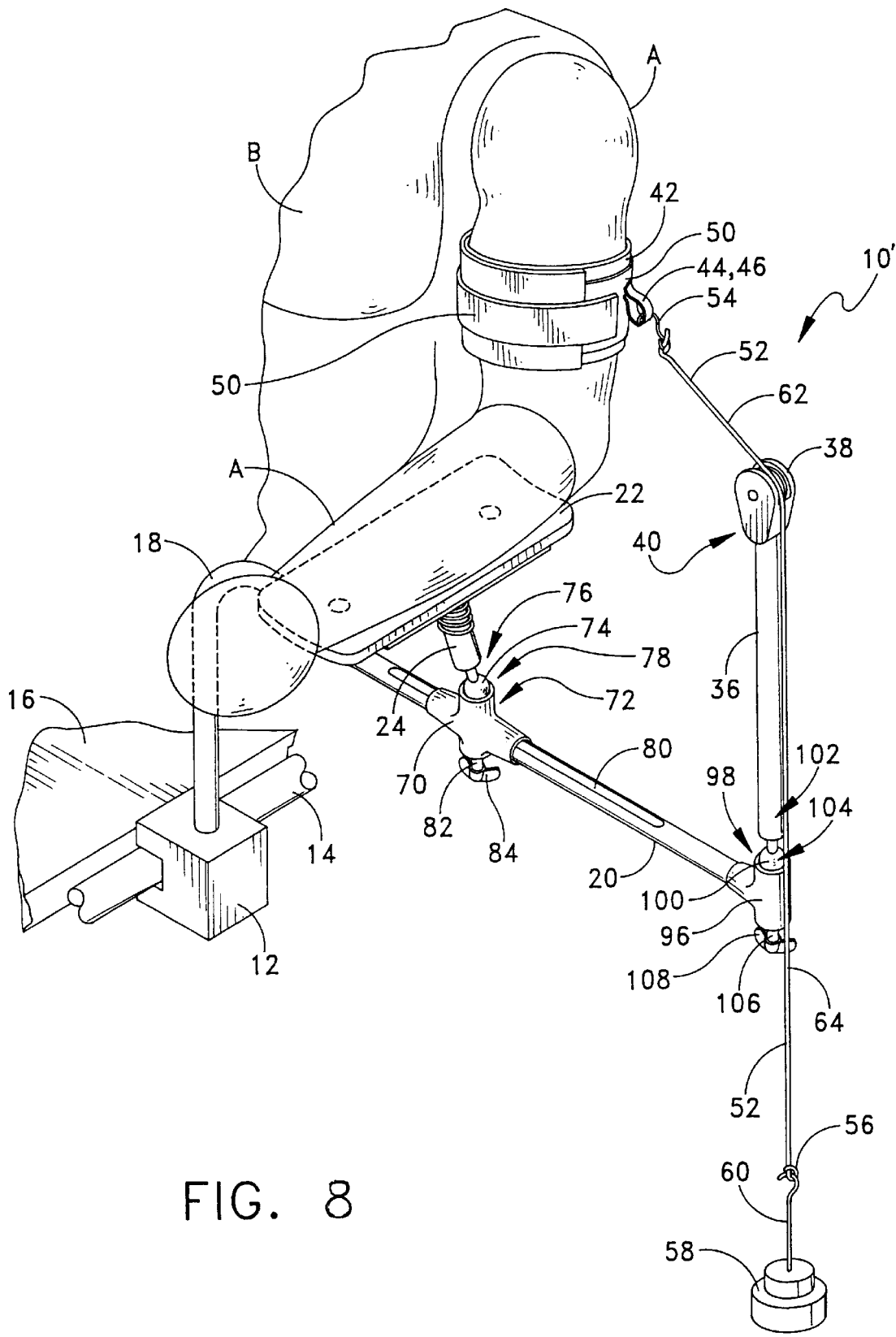
FIG. 8 is a perspective view of another form of apparatus illustrative of an alternative embodiment of the present invention.
Figure 9:
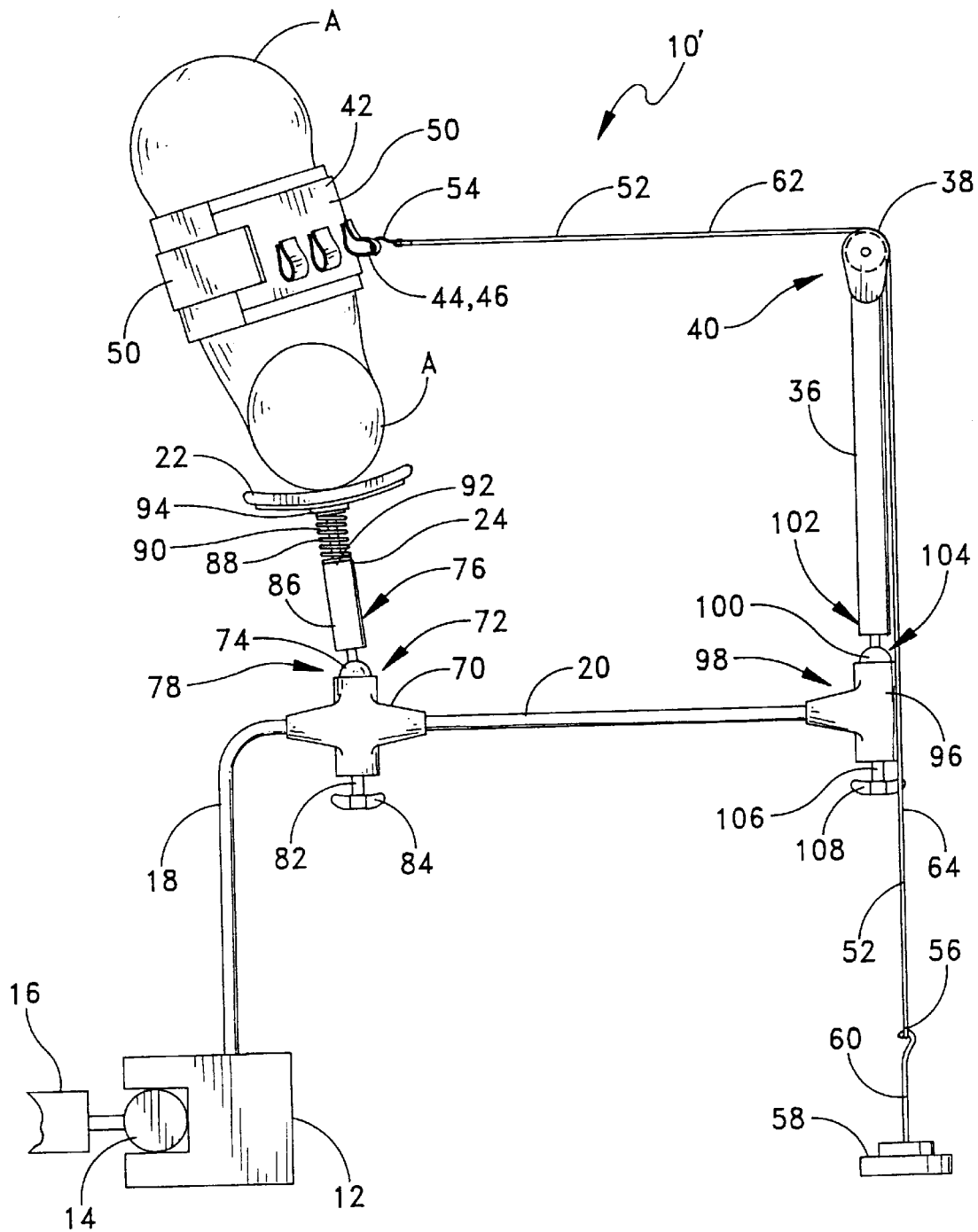
FIG. 9 is a front elevational view of the apparatus of FIG. 8.

Referring next to FIGS. 8 and 9, it will be seen that in an alternative embodiment of apparatus 10', bracket horizontal portion 20 extends through and supports a clamp 70. The clamp 70, at an upper end 72 thereof, retains a ball 74 which is fixed to an end 76 of the forearm pad bar 24. This arrangement essentially defines a ball joint 78 interconnecting forearm pad bar 24 and bracket horizontal portion 20. The bracket horizontal portion 20 is provided with an elongated groove 80 (FIG. 8) in which is disposed a detent (not shown) internally of clamp 70. This groove and detent arrangement permits sliding movement of clamp 70 along bracket portion 20, but prevents rotation of clamp 70 about bracket portion 20. However, ball joint 78 permits movement of pad bar 24, and thereby forearm pad 22, widthwise of bracket portion 20 and rotatively in clamp 70. The clamp 70 is provided with a set screw 82 and handle 84 for locking clamp 70 (including ball 74) in place on bracket portion 20.

The pad bar 24 may comprise a cylinder 86 (FIG. 9) and piston 88, with a coil spring 90 disposed between an upper end 92 of cylinder 86 and a piston head 94 which is fixed to forearm pad 22. Such an arrangement provides a spring support for forearm pad 22. It will be apparent that the cylinder 86 and piston 88 may also be reversed, such that cylinder 86 is fixed to forearm pad 22 and piston head 94 is mounted on bracket portion 20.

In another alternative feature, the end of the bracket's horizontal portion 20 is fixed in a clamp 96 (FIG. 9) retaining, at an upper end 98 thereof, a ball 100 which is fixed to an end 102 of pulley support arm 36. This construction essentially defines a ball joint 104. The pulley support arm 36 is thus movable in clamp 96, which is provided with a set screw 106 and handle 108 for fixing pulley support arm 36 in a selected position in clamp 96.

The use of the apparatus 10' shown in FIGS. 8 and 9 is similar to the manner of use of the embodiment shown in FIGS. 1–7, but fixing of the clamps 70 and 96 requires manipulation of fewer set screw handles.

It should also be appreciated that the spring support for forearm pad 22 which is shown in FIGS. 8 and 9 (i.e., the cylinder 86, piston 88 and coil spring 89) could be incorporated into the embodiment illustrated in FIGS. 1–5.

There is thus provided an apparatus and method for positioning and/or tensioning the arm of a patient undergoing shoulder surgery, wherein the patient may be arranged in a sitting position. The pulling force is applied to the upper arm, and can be applied in an outwardly and downwardly-pulling manner.

It is to be understood that the present invention is by no means limited to the particular constructions and method steps herein disclosed and/or shown in the drawings, but also comprises any modifications or equivalents within the scope of the invention.

What is claimed is:

1. Apparatus for positioning a human arm for shoulder surgery, said apparatus comprising:
   a planar member for receiving, in a sitting position, the human patient to which the arm is appended;
   a clamp fixed to said planar member;
   a bracket mounted on said clamp and having a portion extending laterally from said planar member in a plane generally parallel to the plane of said planar member;
   a pulley support arm connected to said laterally-extending portion of said bracket and extending transversely of said laterally-extending portion and upwardly toward a level generally alongside an upper arm portion of the human arm;
   pulley means mounted on said pulley support arm;
   a cuff for attachment to the upper arm portion of the human arm; and
   a flexible strand adapted, at a first end thereof, for attachment to said cuff, and adapted, at a second end thereof, to receive a selected weight, and adapted between said first and second ends to ride along said pulley means.

2. Apparatus according to claim 1 wherein said laterally-extending bracket portion comprises a continuation of a generally vertically-extending bracket portion mounted in said clamp.

3. Apparatus according to claim 1 and further comprising a forearm pad mounted on said bracket and adapted to support a forearm of the human arm.

4. Apparatus according to claim 3 wherein said pulley support arm is mounted on said laterally-extending bracket portion.

5. Apparatus according to claim 3 wherein said bracket is pivotally movable on said clamp and said laterally-extending bracket portion is movable in a plane parallel to said plane of said planar member.

6. Apparatus according to claim 5 wherein said strand includes a first portion fixed to said cuff and extending therefrom outwardly from the upper arm and a second portion on which said weight is mountable and which depends generally vertically from said first portion, said second portion being a continuation of said first portion.

7. Apparatus according to claim 5 wherein said forearm pad is fixed to a forearm pad bar which is slidably and rotatively disposed in a first tubular clamp, and said first tubular clamp is fixed to a second tubular clamp mounted on said laterally-extending bracket portion, said second tubular clamp being slidable and rotatable on said laterally-extending bracket portion.

8. Apparatus according to claim 7 further comprising a third tubular clamp slidably and rotatively mounted proximate a free end of said laterally-extending bracket portion, said third tubular clamp being fixed to a fourth tubular clamp in which said pulley support arm is slidably and rotatively mounted.

9. Apparatus according to claim 5 wherein said forearm pad is fixed to a first end of a forearm pad bar, said forearm pad bar having a ball at a second end thereof, and a second clamp is slidably and rotatably mounted on said laterally-extending bracket portion and defines a socket in which is disposed said ball so as to define a ball joint interconnecting said forearm pad bar and said laterally-extending bracket portion.

10. Apparatus according to claim 9 wherein said second clamp is provided with a set screw and handle for fixing the position of said forearm pad bar in said second clamp.

11. Apparatus according to claim 10 further comprising an additional clamp mounted on a free end of said laterally-extending bracket portion, said additional clamp having a socket therein, and said pulley support arm having a ball fixed to an end thereof and disposed in said additional clamp socket so as to define a ball joint interconnecting said laterally-extending bracket portion and said pulley support arm.

12. Apparatus according to claim 3 wherein said forearm pad is fixed to a forearm pad bar which is movably connected to said bracket, said forearm pad bar comprising a cylinder and piston assembly wherein one of said cylinder and piston is fixed to said forearm pad and the other of said cylinder and piston is connected to said bracket, said forearm pad bar further comprising a spring for resiliently biasing said piston, and thereby said forearm pad, outwardly from said assembly, so as to provide spring support for said forearm pad.

13. Apparatus according to claim 3 wherein a sterilized, disposable covering is mounted atop said forearm pad.

14. Apparatus according to claim 13 wherein said sterilized, disposable covering comprises a foam rubber type of material.

15. Apparatus according to claim 1 wherein said cuff in provided with a connector thereon for attachment to said strand first end.

16. Apparatus according to claim 15 wherein said connector comprises a plurality of connectors spaced circumferentially around said cuff.

17. Apparatus according to claim 15 wherein said cuff in provided with a series of connectors spaced circumferentially around said cuff.

18. Apparatus for positioning a human arm for shoulder surgery, said apparatus comprising:
   a clamp for attaching said apparatus to a support;
   a bracket pivotally mounted, at an end thereof, on said clamp;

a forearm pad movably mounted on a portion of said bracket removed from said clamp and adapted to support the forearm portion of the human arm;

a pulley support arm movably mounted on said bracket, said pulley support arm extending transversely of said bracket and movable upwardly generally toward an upper arm level of the human arm;

a pulley mounted on said pulley support arm;

an upper arm cuff for attachment to the upper arm portion of the human arm, said upper arm cuff having a connector thereon; and a flexible strand for fixing at a first end thereof to said cuff, for riding along said pulley, and for receiving at a second end thereof a selected weight, a first portion of said strand being adapted for fixing to said cuff connector and for pulling said cuff and thereby the upper arm portion, and a second portion of said strand extending from said pulley and being adapted to receive said weight and to hang downwardly so as to put tension on said strand first portion in response to the pull of gravity on said weight.

19. Apparatus according to claim 18 wherein:

said support comprises a table having a planar top;

said bracket is pivotally movable in a plane parallel with the plane of said table top; and said forearm pad mounted on said bracket is movable thereon toward and away from said table, upwardly and downwardly, and rotatively in two planes.

20. A method for positioning and tensioning a human arm for shoulder surgery, the method comprising the steps of:

providing apparatus comprising a clamp for attaching said apparatus to a support, a bracket pivotally mounted at an end thereof on said clamp, a forearm pad movably mounted on a portion of said bracket removed from said clamp, said forearm pad being adapted to be fastened to a forearm portion of the human arm, a pulley support arm movably mounted on said bracket portion, said pulley support arm extending transversely of said bracket portion and extending upwardly generally toward an upper arm level of the human arm, a pulley mounted on said pulley support arm, an upper arm cuff for attachment to the upper arm portion of the human arm, said upper arm cuff having a connector thereon, a flexible strand for fixing at a first end thereof to said cuff, for riding along said pulley, and for receiving at a second end thereof a selected weight, a first portion of said strand being adapted for fixing to said cuff connector and for pulling said cuff and thereby the upper arm portion, and a second portion of said strand extending from said pulley and being adapted to receive said weight and to hang downwardly so as to put tension on said strand first portion in response to the pull of gravity on said weight;

seating the human on, and attaching the clamp to, the support;

positioning the forearm pad;

supporting the forearm portion of the human arm on the forearm pad;

attaching the upper arm cuff to the upper arm portion of the human arm;

attaching the strand first portion to the cuff and threading the strand through the pulley means; and attaching the selected weight to the strand second portion so as to exert tension on the upper arm portion.

21. A method according to claim 20 including the additional step of moving said pulley support arm axially in a cylindrical clamp fixed to said bracket portion to position said pulley at a selected height.

* * * * *